US 7,015,935 B2

(12) United States Patent
Herget et al.

(10) Patent No.: US 7,015,935 B2
(45) Date of Patent: Mar. 21, 2006

(54) APPARATUS FOR REFERENCE IMAGE ROTATION, AND COMPUTER SOFTWARE PRODUCT AND METHOD FOR REFERENCE IMAGE ROTATION

(75) Inventors: Martin Herget, Erlangen (DE); Martin Harder, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 141 days.

(21) Appl. No.: 09/968,280

(22) Filed: Oct. 1, 2001

(65) Prior Publication Data

US 2002/0071599 A1 Jun. 13, 2002

(30) Foreign Application Priority Data

Sep. 29, 2000 (DE) ............................... 100 48 438

(51) Int. Cl.
*G09G 5/34* (2006.01)
(52) U.S. Cl. ..................................... 345/649; 382/131
(58) Field of Classification Search ................ 345/649, 345/418, 646; 382/131, 132
See application file for complete search history.

(56) References Cited

U.S. PATENT DOCUMENTS

| 4,674,046 A | | 6/1987 | Ozeki et al. | |
|---|---|---|---|---|
| 4,945,478 A | * | 7/1990 | Merickel et al. | 382/131 |
| 5,067,167 A | * | 11/1991 | Berger | 382/277 |
| 5,113,357 A | * | 5/1992 | Johnson et al. | 345/424 |
| 5,309,356 A | * | 5/1994 | Nishide et al. | 382/131 |
| 5,414,623 A | * | 5/1995 | Lu et al. | 382/131 |
| 5,719,498 A | | 2/1998 | Hausmann | |
| 5,734,384 A | * | 3/1998 | Yanof et al. | 345/424 |
| 5,852,646 A | * | 12/1998 | Klotz et al. | 378/8 |

(Continued)

OTHER PUBLICATIONS

Kachelriess, M.; Ulzheimer, S.; Kalender, W.A.; ECG-correlated imaging of the heart with subsecond multislice spiral CT Medical Imaging, IEEE Transactions on , vol.: 19 Issue: 9 , Sep. 2000 Page(s): 888-901.*

Saeed, N.; Durrani, T.S.; A new MRI rotation algorithm for the registration of temporal images, Acoustics, Speech, and Signal Processing, 1989. ICASSP-89., 1989 International Conference on , May 23-26, 1989 Page(s): 1496-1499 vol. 3.*

(Continued)

*Primary Examiner*—Michael Razavi
*Assistant Examiner*—J. Amini
(74) *Attorney, Agent, or Firm*—Schiff Hardin LLP

(57) ABSTRACT

In an apparatus for displaying reference images of patients and slices to be measured in a displayed reference image for assisting the positioning of slices in preparation for a slice-by-slice measurement and a computer software product and corresponding method, a storage device stores at least one measured reference image of a current patient, a display screen displays a stored reference image, an input device allows entry of commands for displaying and positioning slices to be measured in a displayed reference image, and a processing device processes the entered commands and correspondingly controls the display of the reference image and the slices. The processing device, depending on the entry of commands via the input device by a user, generates a rotated representation of the reference image and a spatial representation—corresponding to the rotation of the reference image—of the slices and displays them on the screen.

21 Claims, 2 Drawing Sheets

U.S. PATENT DOCUMENTS 6,144,384 A * 11/2000 Nakazawa ............... 345/424
6,181,766 B1 * 1/2001 Pearson et al. ........... 378/15
6,243,436 B1    6/2001 Hahn et al.
6,421,454 B1 * 7/2002 Burke et al. ............. 382/131
6,438,260 B1 * 8/2002 Robinson ................. 382/131

OTHER PUBLICATIONS

"Interactive Display and Analysis of 3-D Medical Images," Robb et al., IEEE Trans. on Mag. Imaging, vol. 8, No. 1, Sep. 1999, pp 217-226.

* cited by examiner

APPARATUS FOR REFERENCE IMAGE ROTATION, AND COMPUTER SOFTWARE PRODUCT AND METHOD FOR REFERENCE IMAGE ROTATION

BACKGROUND OF THE INVENTION

1. Field of the Invention

The present invention relates to an apparatus for representing reference images of patients, and slices to be registered in a represented reference image, for assisting the positioning of slices in preparation for a slice-by-slice data-acquisition, and to a computer software product for an apparatus of this type.

2. Description of the Prior Art

In so-called graphical slice positioning (GLP) to prepare for measurements and examinations by means of a magnetic resonance imaging apparatus, slices to be newly measured are planned on already measured images of a current patient. In this case, one or a plurality of so-called reference images of the current patient's body parts to be examined are recorded by the magnetic resonance imaging apparatus and represented on a screen. The slice-by-slice measurements to be carried out in the corresponding body part by means of the magnetic resonance imaging apparatus are planned using the represented reference image or images. In this case, the slices or slice groups are supplied to the corresponding data processing apparatus (such as e.g. a computer) by the competent doctor or the person carrying out the examination, via an input apparatus, such as e.g. a keyboard and/or a mouse, and are displayed directly in the represented reference image on the screen of the data processing apparatus. In this case, the slices or slice groups can be arbitrarily inclined and rotated in order to be able to obtain the desired images using the later measurement.

In the known methods and apparatuses for graphical slice positioning, positioning of the slices is possible in a maximum of three difference reference images of the body part to be examined. The accompanying FIGS. 2a and 2b represent, as an example, two different views as reference images of a patient's head to be examined. FIG. 2a shows, as the first reference image, a left side view of a sectional image of the head (sagittal image) and FIG. 2b shows, as the second reference image, a front view of a sectional image of the head (coronary image). The second reference image of FIG. 2b is therefore rotated through 90° relative to the first reference image of FIG. 2a.

Also shown is a slice group formed by a number of slices 11 which were entered by a user into the corresponding data processing apparatus. The slices 11 of the slice group are doubly inclined. In the first reference image shown in FIG. 2a, the inclination of the slices as proceeding from the rear side of the head toward the face can be readily discerned. In the second reference image represented in FIG. 2b, it can be seen that the slices 11 of the slice group also are inclined in a manner proceeding from the left side of the head toward the right side of the head. From a technical standpoint, as represented for example in FIGS. 2a and 2b, the planned slices 11 of a slice group are represented in the form of sectional or projection lines in the reference images. The type of representation is distinguished as sectional lines or as projection lines by means of an automatic facility in the processing apparatus using the angular position of the planned slices relative to the respective reference image. Oblique and doubly oblique slices are represented by dashed sectional lines, as is shown for example in FIGS. 2a and 2b. Perpendicular slices are represented by a solid sectional line.

In the corresponding software for image processing, the orientation of a slice is described in text form by means of a so-called history string, also called an orientation string. However, this description has a major disadvantage, namely that the sign rule for determining the direction of rotation, i.e. positive or negative, is very complicated and the risk of errors is correspondingly high.

As mentioned above, the known apparatuses and methods for representing reference images of graphic slice positioning enable only the representation of two to a maximum of three reference images. Although the slices, such as e.g. the slices 11 of the slice group represented in FIGS. 2a and 2b, can be freely displaced and rotated via a corresponding input apparatus of the assigned data processing system, it is difficult even for practiced users to correctly interpret the actual position of the slices using the depicted sectional or projection lines in the reference images. That holds true in particular when the planned slices are doubly oblique relative to the reference images used or when the slices associated with a slice group only partly penetrate the reference image. As illustrated in FIGS. 2a and 2b, doubly oblique slices arise e.g. when a user rotates an originally transverse or horizontal slice group firstly in a sagittal reference image, such as e.g. the first reference image, around the vertical sectional line 12a and then in the coronary reference image, such as e.g. the second reference image of FIG. 2b, around the other vertical sectional line 12b.

In these cases of doubly inclined slice groups, which occur very often in cardiology and orthopedics, a high degree of spatial imagination is necessary in order to understand the actual situation behind, in some instances, the very shapeless sectional line representations, and in particular in order to assess whether the planned slices represented in the reference images actually cover the region or body part to be measured or to be examined.

Usually, according to the prior art, the user has to carry out a number of iteration steps until he or she actually arrives at the desired slice orientation required for the examination. In this case, generally an overview measurement or so-called localizer measurement is carried out initially, and then one or more further positioning processes and measurements. The result images of each measurement are in each case used for further positioning of the slices. However, since the reference images of the localizer measurements in each case represent only one sectional view and a maximum of three reference images can be used for positioning the slices, often a number of attempts have to be made one after the other before the region to be examined is represented ideally on the resultant images of a measurement, i.e. before the optimum slice position and orientation has been found.

SUMMARY OF THE INVENTION

An object of the present invention is to provide an apparatus for representing reference images of patients and slices to be measured in a displayed reference image for assisting the positioning of slices in preparation for a slice-by-slice measurement, and a corresponding computer software product for an apparatus of this type, which enable a user to position slices to be measured in a displayed reference image by means of an improved display in a simple manner.

This object is achieved in an apparatus for representing reference images of patients and slices to be measured in a displayed reference image for assisting the positioning of slices in preparation for a slice-by-slice measurement in having a storage device for storing at least one measured reference image of a current patient, a screen for displaying a stored reference image, an input device for entering commands for displaying and positioning slices to be measured in a displayed reference image, and a processing device for processing the entered commands and corresponding control of the display of the reference image and the slices. The processing device, depending on the entry of corresponding commands via the input device by a user, generates a rotated representation of the reference image and a spatial representation—corresponding to the rotation of the reference image—of the slices and displaying them on the screen.

The above object is furthermore achieved by a computer software product for an apparatus of this type which is suitable for carrying out the following steps: processing commands that have been entered for representing and positioning slices to be measured in a reference image displayed on a screen, and corresponding control of the representation of the reference image and the slices, in which case, depending on the entry of corresponding commands by a user, a rotated representation of the reference image and a spatial representation—corresponding to the rotation of the reference image—of the slices are generated and displayed on the screen.

The apparatus according to the invention and the computer software product according to the invention enable a user to effect a significantly simplified positioning of slices to be measured with regard to a patient's body part to be measured, by means of a significantly improved display on the screen. Through the possibility of rotating the reference image together with the selected slices and the corresponding spatial representation of the slices, the position of the slices with regard to the reference image of the body part to be measured is visualized for the user in an extremely simple manner. In particular, the user can rotate the reference image as desired and observe the position of the slices from very different angles. This results in a series of major advantages for the user. The user understands the spatial relationships between the positioned slices and the reference image or the body part to be examined significantly faster. This saves a great deal of time which is required in conventional systems in order to conceptually reconstruct a spatial image using the sectional lines of the slices or in order to iteratively correct erroneous measurement and repeat it. Furthermore, the transition between different views of a spatial situation can easily be understood since the reference image together with the spatial representation of the slices can be adjusted practically in a continuously variable manner. The probability of slices being incorrectly positioned and therefore of an incorrect measurement being carried out is minimized. This makes it possible to minimize the burdens on the patient on account of the measurements both as to the examination time and the radiated energy. That is advantageous in particular in the case of magnetic resonance imaging examinations, which are very cost-intensive. Furthermore, the handling of the apparatus according to the invention and of the computer software product according to the invention is simple and easy to learn even for users who are not specially trained, and can be technically fully integrated into existing systems for graphical slice positioning. In this case, it is particularly advantageous that the effects of a change in the slices or the inclination thereof can immediately be visualized as to their effects with regard to the body part to be examined.

In an advantageous manner, the processing device generates a frame around the reference image and generates the rotated representation of the reference image with the frame as a rotated two-dimensional structure and represents the rotated representation of the reference image on the screen. Since the reference image has actually been measured, and is represented, as a two-dimensional structure, the frame advantageously serves to visualize the rotation of the reference image. The reference image is generally rotated about a center axis which, for example, may simultaneously be the sectional axis of a further reference image. The reference image can be rotated for example about a vertical center axis or else about a horizontal center axis. Furthermore, it is possible to rotate the reference image around arbitrarily inclined axes in order to visualize the spatial arrangement of the slices.

Furthermore, it is advantageous if the processing device generates the rotated representation of the reference image and of the frame depending on the direction of rotation in a perspective view and represents it on the screen. In this case, the perspective view is not a genuine perspective view with a larger-smaller representation from front to back, but rather a type of parallel projection of the reference image on the corresponding angle of rotation or inclination. However, the perspective representation can be greatly assisted by the frame if the latter is likewise represented in a perspective manner, i.e. if the upper and lower edges of the frame converge toward the rear.

In an advantageous manner, the spatial representation of the slices which is generated by the processing device is a three-dimensional representation of the contour lines of the entire slice group. In this case, the three-dimensional representation of the contour lines may have the form of a parallelepiped, the parallelepiped advantageously being shaped as a cuboid. Through the three-dimensional representation of the contour lines of the slice group, the spatial relationship between the arrangement of the slices of the slice group and the reference image is clarified to the user in any position of the reference image.

In an advantageous manner, the processing device represents in a distinguishable fashion the contour lines which face the observer when represented on the screen and the contour lines which are hidden to the observer. In this case, it is advantageous, in particular, if the contour lines which face the observer are represented in a visible fashion and the contour lines which are hidden to the observer are represented in an invisible fashion. The contour lines which are hidden to the observer are those contour lines of the slice group which, as it were, are concealed by the areas—facing the observer—of the three-dimensional representation of the contour lines. Furthermore, it is advantageous if the processing device does not represent the contour lines which lie behind the reference image including the frame when represented on the screen for the observer. These measures significantly reinforce the spatial effect of the representation.

The computer software product according to the invention is suitable for loading for example into a memory of a processing apparatus, such as e.g. a computer, in order to be executed there. In this case, the corresponding processing steps can be carried out by means of a microprocessor or another suitable control device.

DESCRIPTION OF THE PREFERRED EMBODIMENTS

Figure 1:
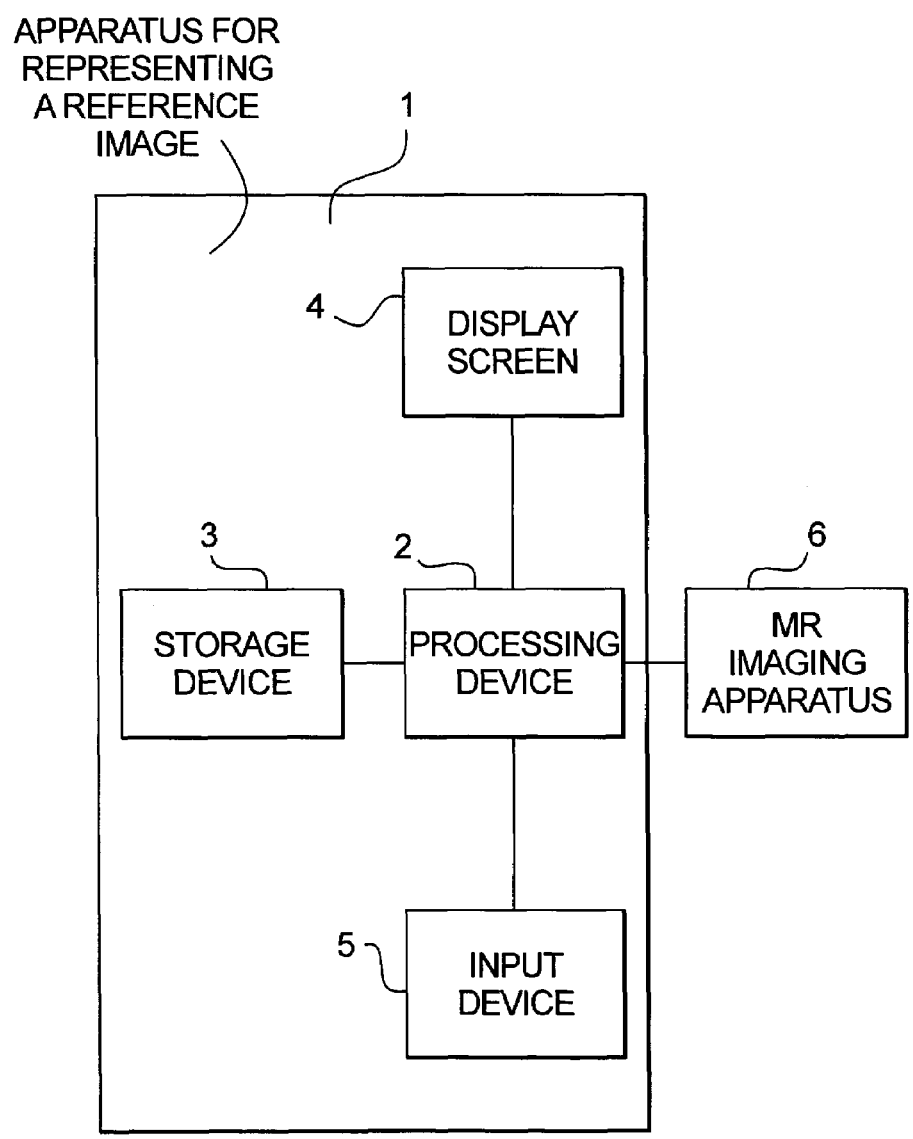
FIG. 1 is a schematic representation of an apparatus according to the invention for representing reference images and slices to be measured.

FIG. 1 is a schematic illustration of an apparatus 1 according to the invention for representing reference images of patients and slices to be measured in a displayed reference image for assisting the positioning of slices in preparation of a slice-by-slice measurement, for example by means of a magnetic resonance imaging apparatus 6. The apparatus 1 according to the invention is, for example, a data processing apparatus, such as a computer or the like, and comprises a processing device 2, a storage device 3, a screen 4 and an input device 5. Of course the apparatus 1 according to the invention has all further elements required for proper operation, such as e.g. clock generator, power supply, etc, however, these are not crucial for the functions according to the invention, and therefore are not represented for clarity.

The apparatus 1 according to the invention serves for displaying reference images and slice groups in order to prepare for an examination of a patient in a magnetic resonance imaging apparatus 6. In this case, in the magnetic resonance imaging apparatus, at least one reference image is recorded as a sectional image of the patient's body part to be examined and is stored in the storage device 3. Afterward, the user, i.e. the competent doctor or the person conducting the examination, plans the further measurement using the reference image displayed on the screen 4. Since a slice-by-slice measurement takes place in magnetic resonance imaging examinations, a user plans the position of the slices to be examined with regard to the reference image by choosing and setting a corresponding slice group.

One example of a reference image of this type is shown in FIG. 2a. The reference image in FIG. 2a is a sectional image through the head 10 of a patient and, more precisely, represents a longitudinal section along the symmetrical center plane of the head. By way of example, a number of slices 11, as slice group to be measured, are depicted by dashed lines. Furthermore, a vertical sectional line 12a is of the reference image represented in FIG. 2a. The corresponding sectional view shows the second reference image, which is shown in FIG. 2b. FIG. 2b therefore shows a sectional view of the patient's head in the transverse plane. As can be seen in FIGS. 2a and 2b, the slices 11 of the slice group to be measured are doubly obliquely inclined, e.g. both in the longitudinal plane and in the transverse plane. The vertical sectional line 12b in FIG. 2b is the sectional plane of the representation of FIG. 2a. As mentioned in the introduction to the description, FIGS. 2a and 2b are examples of reference images which are used for the known graphical slice positioning and in which the user can position the slices.

According to the present invention, by way of example, a reference image, such as e.g. the reference image shown in FIG. 2a, serves as the starting point for the representation and positioning of the slices 11 in the displayed reference image. According to the present invention, a rotated representation of the reference image and a spatial representation of the slices which corresponds to the rotation of the reference image are generated for the user and represented on the screen 4 of the apparatus 1. Various stages of the reference image rotation according to the invention are shown in FIGS. 2c to 2g. The starting point is the reference image—shown in FIG. 2a—of a longitudinal section of the patient's head 10 with the slices 11 which are arranged and entered by the user via the input device 3, such as e.g. a keyboard and/or a mouse. The slices 11 are shown as dashed sectional lines in the reference image 2a.

After a user has entered a corresponding command via the input device 5, the reference image is represented in a rotated fashion. To that end, after the entry of the command at the input device 5, the command is processed by the processing device 2 in that a reference image representation which is rotated in accordance with the command is generated as a two-dimensional projection and provided with a corresponding frame 13. FIGS. 2c to 2g show a corresponding rotated representation of the reference image of the head 10 from FIG. 2a with an in each case larger angle of rotation. In this case, the processing device 2 does not generate a real perspective view of the head 10 but rather a two-dimensional projection. The angle of rotation is assisted by the frame 13 placed around the head 10, which frame is represented in a correspondingly perspective fashion with increasing angle of rotation and visualizes the angle of rotation for the user. At the same time, the processing device 2 generates a spatial representation of the slices 11 which corresponds to the rotation of the reference image, in that the contour lines 14 of the slice group are represented as a cuboid. In this case, the cuboid form is only one of various spatial representation forms that are possible.

As can readily be discerned in FIGS. 2d to 2g, in the exemplary embodiment represented here the contour lines of those contour lines of the cuboid 14 which face the user are represented. These so-called hidden contour lines are not represented. As an alternative, the hidden contour lines may be represented such that they are indeed visible but, for example, darker than the contour lines which face the user. Furthermore, in order to support the three-dimensional effect, those contour lines of the cuboid 14 which lie behind the frame 13 are cut out and not represented.

The represented image sequence 2a, 2c, 2d, 2e, 2f represents a rotation of the saggital reference image of the head 10 (FIG. 2a) through about 90°. According to the image shown in FIG. 2f, it is possible to show either the corresponding coronary image, as is represented for example in FIG. 2b, or the view that is correspondingly rotated further is represented, as is shown for example in FIG. 2g.

The image sequence 2a to 2g shows a rotation of the reference image of the head 10 about the vertical axis 12a, which represents the sectional plane for the coronary view of FIG. 2b. It goes without saying that the reference image can, according to the invention, also be rotated in any other direction, for example in the horizontal direction. The selection of the direction of rotation or of the axis of rotation via the mouse as input device is appropriate in this case. Directly after the initiation of the rotation proceeding from the respective reference image, the frame and the spatial representation of the slice group appear as a projection in the respective observer plane or plane of the screen 4 of the apparatus 1 according to the invention. By moving the mouse to and fro, the angle of rotation of the reference image is respectively changed in this case and the projection of the reference image including the frame and the spatial representation of the slice group is calculated anew by the processing device 2 and represented on the screen 4. The spatial situation between the slice group planned for the measurement and the reference image used therefore can be observed three-dimensionally practically from all sides. In particular, the sectional and projection lines of a slice group appear spatially all at once and are thus significantly easier to assign to the body part to be measured. In particular, the angles of inclination and sectional angles of the slices 11 of the slice group with regard to the body part to be measured can also be detected rapidly and the desired position of the slices for the subsequent measurement can therefore be determined simply and efficiently.

In the embodiments shown in FIGS. 2a to 2g, the frame is not represented in the reference image of FIG. 2a, which forms the starting point, and does not appear until there is slight rotation. If the reference image is rotated from one of the positions of FIG. 2c to FIG. 2g back into the starting position of FIG. 2a, the frame disappears again. As an alternative, it would also be conceivable here for the reference image already to be surrounded by a frame in the starting state. This configuration would possibly be advantageous in conjunction with inputting of the rotation commands exclusively via a computer mouse as input device 5, since the frame could be clicked on directly by the mouse and rotated in order to obtain a spatial representation of the slice group. Furthermore, it would be advantageous for specific applications if the observer, after the selection and positioning of the slices 11 of the slice group in the reference image which serves as a starting point, were shown an automated moving animation of the rotation of the reference image, in which the reference image rotates independently at a specific selectable speed through a specific selectable angle.

Figure 2:
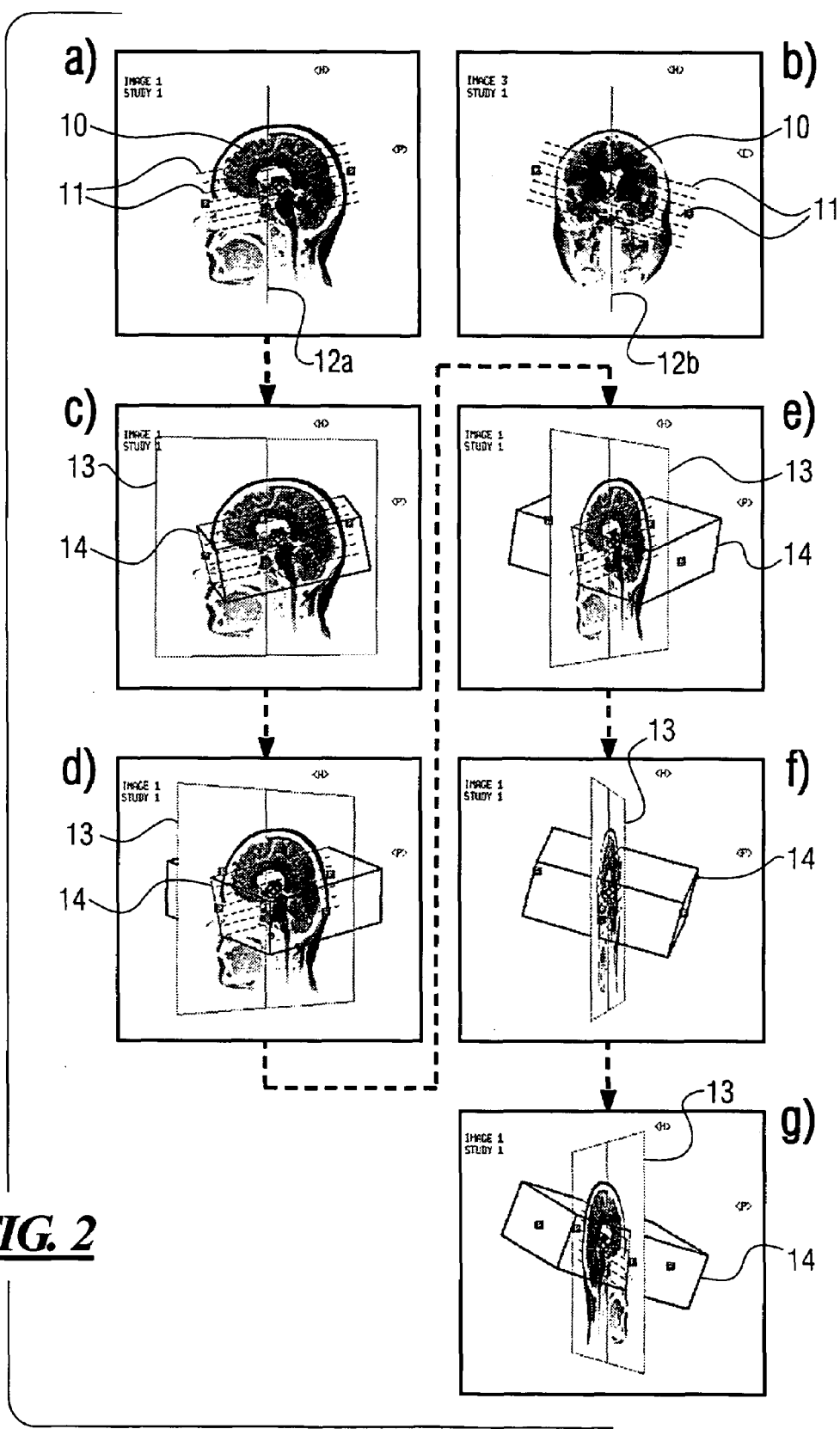
FIGS. 2a through 2g show representations of reference images and slices to be measured.

As briefly mentioned above, for fulfilling the functions according to the invention, a single reference image, such as e.g. the reference image of FIG. 2a, is sufficient for the visualization of the positioning of the slices 11 to be measured with regard to the body part to be examined, since, by way of example, the representation sequence of FIG. 2c to FIG. 2g already conveys to the observer an extensive documentation of the relative position of the slices with respect to the body part to be examined. However, if a second image or further reference images is or are present, such as e.g. a coronary view as shown in FIG. 2b, it or they could be inserted at a corresponding point into the sequence of rotated reference images. In the example shown in FIG. 2, the coronary sectional image of the head 10 as shown in FIG. 2b could therefore be inserted in the transition between the representations of FIGS. 2f and 2g. In this case, the sectional lines of the slices 11 of the sectional group should also be depicted in this image and the spatial representation of the slices, the cuboid 14 in the present case, would have to be reduced to the contour lines facing the observer before the inserted sectional image.

Furthermore, it must be emphasized that the complete functionality for selection and positioning of the slices 11 is also available to the user in every rotated position of the reference image, such as e.g. in every position of FIGS. 2c to 2g. As an alternative, the rotated representation of the reference image could be coupled to the mouse movement in such a way that when the mouse is released, the image automatically returns to the starting position such as e.g. the position of FIG. 2a, and that the slices can be positioned by the user only in this position.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for displaying a reference image of a subject, and slices of said subject to be measured in the displayed reference image, for individually positioning two-dimensional slices in preparation for a subsequent slice-by-slice measurement of said subject, comprising:

a storage device for storing at least one reference image of current patient;

a display screen for displaying the stored reference image as a two-dimensional structure;

an input device for entering commands for displaying and positioning slices of said current patient to be measured, in the displayed reference image;

a processing device connected to said storage device, said display screen and said input device, for processing the commands entered via said input device and for controlling display of said reference image and said slices on said display screen, said processing device, dependent on the commands entered via said input device, generating a perspectively rotated representation of said reference image and a spatial representation, indication corresponding to the perspective rotation of the reference image, of said layers, and causing said perspectively rotated representation to be displayed on said display screen together with said spatial representation indication, said processing device generating a perspectively rotatable frame around said reference image on said display screen as said spatial representation indication, and generating the perspectively rotated representation of said reference image together with said perspectively rotated frame as an at least two-dimensional structure on said screen that is rotated in a same direction as said perspectively rotated representation of said reference image.

2. An apparatus as claimed in claim 1 wherein said processing device generates said frame as a three-dimensional representation of contour lines of a group of layers.

3. An apparatus as claimed in claim 2 wherein said processing device generates said frame as a parallelepiped.

4. An apparatus as claimed in claim 3 wherein said processing device generates a cuboid as said parallelepiped.

5. An apparatus as claimed in claim 2 wherein said processing device causes respective contour lines to be displayed on said display screen so that contour lines facing an observer of said display screen are distinguishable from contour lines which are hidden from said observer.

6. An apparatus as claimed in claim 2 wherein said processing device causes contour lines which face an observer of said display screen to be visibly displayed, and makes contour lines which are hidden to an observer invisible on said display screen.

7. An apparatus as claimed in claim 2 wherein said processing device inhibits representation of contour lines which lie behind said reference image on said display screen, including said frame, as seen by an observer of said display screen.

8. A computer readable medium encoded with a computer program for operating a processing unit for displaying a reference image of a subject, and two-dimensional slices of said subject to be measured in the displayed reference image, for positioning two-dimensional slices in preparation for a subsequent slice-by-slice measurement of said subject, said processor unit being connected to a storage device for storing at least one reference image of a current patient a display screen for displaying the stored reference image as a two-dimensional structure, and an input device for entering commands for displaying and positioning layers of said current patient to be measured, in the displayed reference image, said computer readable medium encoded with a computer program operating said processing device, for processing the commands entered via said input device and for controlling display of said reference image and said layers on said display screen, so that said processing device, dependent on the commands entered via said input device, generates a perspectively rotated representation of said reference image and a spatial representation indication, corresponding to the perspective rotation of the reference image, of said layers, and causes said perspectively rotated representation to be displayed on said display screen together with said spatial representation indication and said computer readable medium encoded with a computer program operating said processing device to generate a perspectively rotatable frame around said reference image on said display screen as said spatial representation indication, and to generate said perspectively rotated representation of said reference image together with the perspectively rotated frame as a rotated, at least two-dimensional structure on said display screen that is rotated in a same direction as said perspectively rotated representation of said reference image.

9. A computer readable medium encoded with a computer program as claimed in claim 8 which operates said processing device to generate said frame as a three-dimensional representation of contour lines of a group of layers.

10. A computer readable medium encoded with a computer program as claimed in claim 9 which operates said processing device to generate said frame as a parallelepiped.

11. A computer readable medium encoded with a computer program as claimed in claim 10 which operates said processing device to generate a cuboid as said parallelepiped.

12. A computer readable medium encoded with a computer program as claimed in claim 9 which operates said processing device to cause respective contour lines to be displayed on said display screen so that contour lines facing an observer of said display screen are distinguishable from contour lines which are hidden from said observer.

13. A computer readable medium encoded with a computer program as claimed in claim 9 which operates said processing device to cause contour lines which face an observer of said display screen to be visibly displayed, and makes contour lines which are hidden to an observer invisible on said display screen.

14. A computer readable medium encoded with a computer program as claimed in claim 9 which causes said processing device to inhibit representation of contour lines which lie behind said reference image on said display screen, including said frame, as seen by an observer of said display screen.

15. A method for displaying a reference image of a subject, and slices of said subject to be measured in the displayed reference image, for positioning two-dimensional slices in preparation for a subsequent slice-by-slice measurement of said subject, comprising the steps of:
storing at least one reference image of current patient in a storage device;
providing a display screen for displaying the stored reference image as a two-dimensional structure;
entering commands for displaying and positioning slices of said current patient to be measured, in the displayed reference image, via an input device;
connecting a processing device to said storage device, said display screen and said input device, and processing the commands entered via said input device and for controlling display of said reference image and said layers on said display screen, and in said processing device, dependent on the commands entered via said input device, generating a perspectively rotated representation of said reference image and a spatial representation indication, corresponding to the perspective rotation of the reference image, of said layers, and causing said perspectively rotated representation to be displayed on said display screen together with said spatial representation indication, said processing device generating a perspectively rotatable frame around said reference image on said display screen as said spatial representation indication, and generating said perspectively rotated representation of said reference image together with the perspectively rotated frame as a rotated, at least two-dimensional structure on said display screen that is rotated in a same direction as said perspectively rotated representation of said reference image.

16. A method as claimed in claim 15 comprising, in said processing device, generating said frame as a three-dimensional representation of contour lines of a group of layers.

17. A method as claimed in claim 16 comprising, in said processing device, generating said frame as a parallelepiped.

18. A method as claimed in claim 17 comprising, in said processing device, generating a cuboid as said parallelepiped.

19. A method as claimed in claim 16 comprising, via said processing device, causing respective contour lines to be displayed on said display screen so that contour lines facing an observer of said display screen are distinguishable from contour lines which are hidden from said observer.

20. A method as claimed in claim 16 comprising, via said processing device, causing contour lines which face an observer of said display screen to be visibly displayed, and makes contour lines which are hidden to an observer invisible on said display screen.

21. A method as claimed in claim 16 comprising, via said processing device, inhibiting representation of contour lines which lie behind said reference image on said display screen, including said frame, as seen by an observer of said display screen.

* * * * *